(12) United States Patent
Sakamoto et al.

(10) Patent No.: US 10,509,027 B2
(45) Date of Patent: Dec. 17, 2019

(54) URINE SAMPLE ANALYZER AND URINE SAMPLE ANALYZING METHOD

(71) Applicant: SYSMEX CORPORATION, Kobe-shi, Hyogo (JP)

(72) Inventors: Mitsumasa Sakamoto, Kobe (JP); Shota Tateyama, Kobe (JP); Masanori Kawano, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 89 days.

(21) Appl. No.: 15/241,123

(22) Filed: Aug. 19, 2016

(65) Prior Publication Data

US 2017/0059560 A1 Mar. 2, 2017

(30) Foreign Application Priority Data

Aug. 28, 2015 (JP) .................................. 2015-169861

(51) Int. Cl.
   *G01N 33/52* (2006.01)
   *G01N 15/14* (2006.01)
   (Continued)

(52) U.S. Cl.
   CPC ......... *G01N 33/52* (2013.01); *G01N 15/1429* (2013.01); *G01N 15/1459* (2013.01); *G01N 33/493* (2013.01); *G01N 33/80* (2013.01); *G01N 2015/1006* (2013.01); *G01N 2015/1488* (2013.01); *G01N 2015/1497* (2013.01)

(58) Field of Classification Search
   CPC ...... G01N 33/52; G01N 33/80; G01N 33/493; G01N 15/1429; G01N 15/1459; G01N 2015/1488; G01N 2015/1497; G01N 2015/1006
   See application file for complete search history.

(56) References Cited

U.S. PATENT DOCUMENTS 5,731,867 A  3/1998 Katayama
2001/0024806 A1  9/2001 Matsumoto et al.
(Continued)

FOREIGN PATENT DOCUMENTS

CN  1159583 A  9/1997
CN  104020282 A  9/2014
(Continued)

OTHER PUBLICATIONS

David A Benaron et al., Quantification of Mammalian Sperm Morphology by Slit-Scan Flow Cytometry, Cytometry, 1982, pp. 344-349, vol. 2, No. 5, Alan Liss, New York, USA. (Cited in EESR).
(Continued)

*Primary Examiner* — Dennis White
(74) *Attorney, Agent, or Firm* — Metrolex IP Law Group, PLLC

(57) ABSTRACT

A urine sample analyzer is disclosed. A measurement specimen containing a urine sample flows through flow cell, and light is applied to the measurement specimen flowing through flow cell. Then, a signal corresponding to light received from particles contained in the urine sample is acquired. Thereafter, presence of sperms in the urine sample is analyzed based on parameters reflecting the waveform of the acquired signal.

13 Claims, 14 Drawing Sheets

(51) Int. Cl.
*G01N 33/80* (2006.01)
*G01N 33/493* (2006.01)
*G01N 15/10* (2006.01)

(56) References Cited

U.S. PATENT DOCUMENTS

| | | |
|---|---|---|
| 2007/0254331 A1 | 11/2007 | Kawashima |
| 2009/0323062 A1* | 12/2009 | Ariyoshi ............ G01N 15/1459 356/337 |
| 2011/0008767 A1 | 1/2011 | Durack |
| 2011/0149287 A1* | 6/2011 | Kislev .................... B01L 3/502 356/436 |
| 2014/0242633 A1 | 8/2014 | Fukuda et al. |
| 2014/0273192 A1* | 9/2014 | Sharpe .............. B01L 3/502761 435/288.7 |
| 2015/0369741 A1 | 12/2015 | Ozasa et al. |

FOREIGN PATENT DOCUMENTS

| | | |
|---|---|---|
| CN | 104568844 A | 4/2015 |
| JP | 2002-277381 A | 9/2002 |
| JP | 2007-255954 A | 10/2007 |
| JP | 2015-87176 A | 5/2015 |
| WO | 2014/086375 A1 | 6/2014 |
| WO | 2014/133160 A1 | 9/2014 |

OTHER PUBLICATIONS

The Chinese office action dated May 8, 2019 in a counterpart Chinese patent application.
A Chinese Office Action (CNOA) dated Sep. 26, 2019 in a counterpart Chinese patent application.

* cited by examiner

NO SPERMS

SPERMS PRESENT

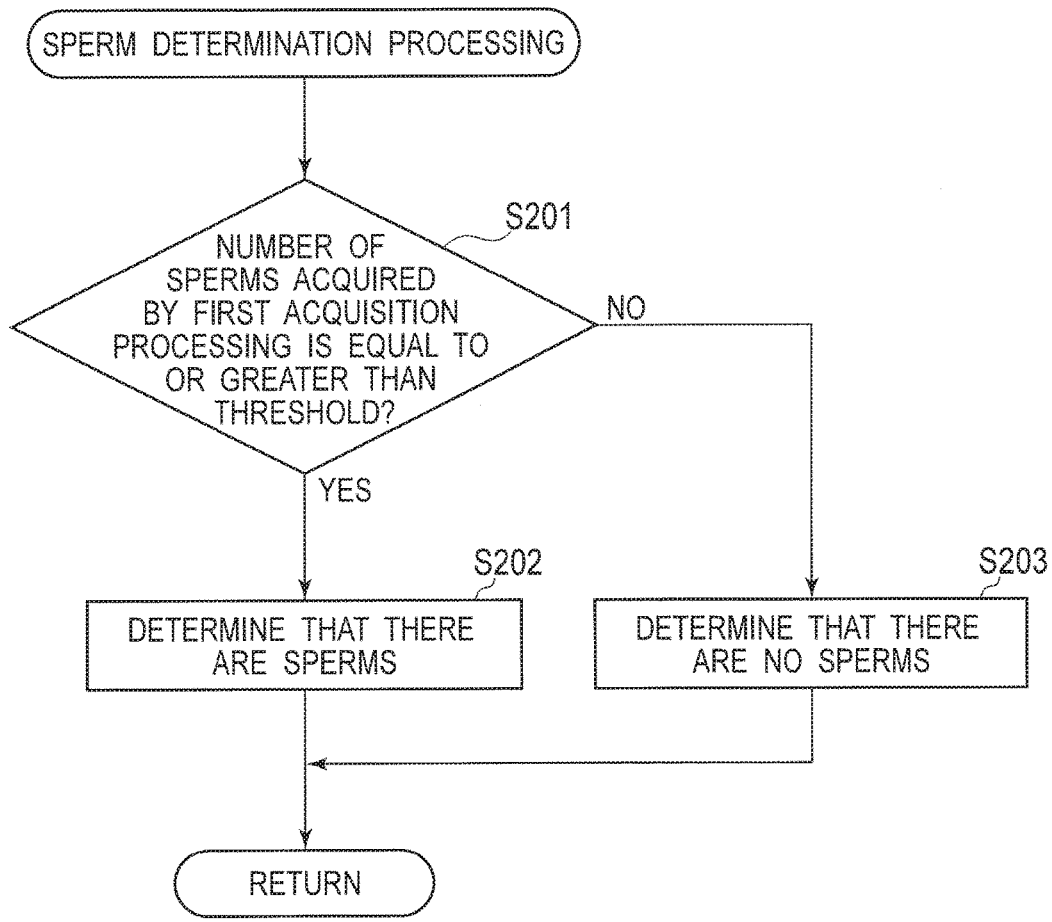

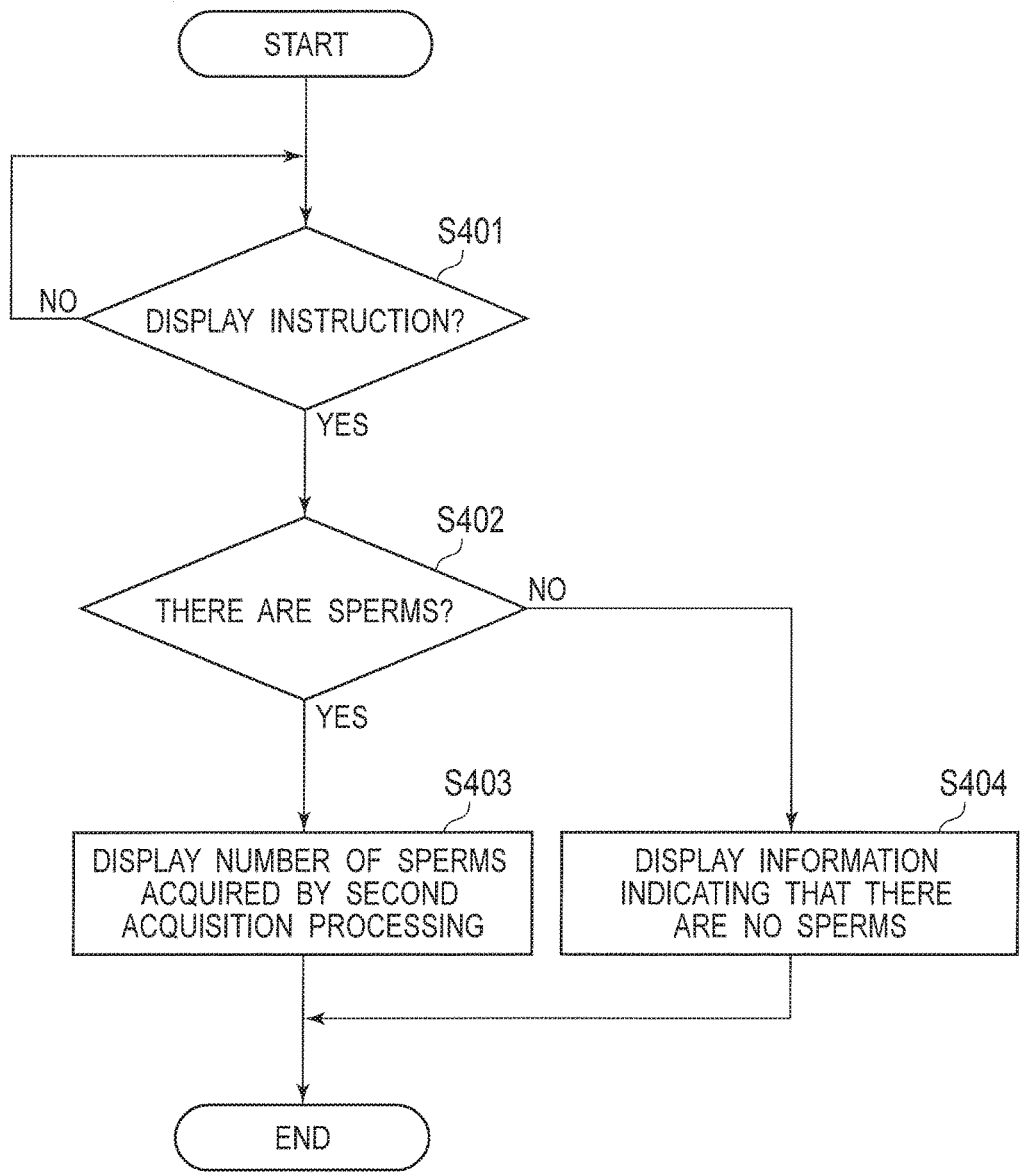

FIG. 11A

| COMPARATIVE EXAMPLE | SPERMS PRESENT | 222 | 12 |
|---|---|---|---|
| | NO SPERMS | 364 | 0 |
| | | NO SPERMS | SPERMS PRESENT |
| | | VISUAL OBSERVATION | |

FIG. 11B

| COMPARATIVE EXAMPLE | SENSITIVITY | 100.0% |
|---|---|---|
| | SPECIFICITY | 62.1% |

FIG. 11C

| COMPARATIVE EXAMPLE | NUMBER OF EXACT MATCHES | 376 |
|---|---|---|
| | EXACT MATCH RATE | 62.9% |

FIG. 12A

| EMBODIMENT 1 | SPERMS PRESENT | 0 | 10 |
|---|---|---|---|
|  | NO SPERMS | 586 | 2 |
|  |  | NO SPERMS | SPERMS PRESENT |
|  |  | VISUAL OBSERVATION | |

FIG. 12B

| EMBODIMENT 1 | SENSITIVITY | 83.3% |
|---|---|---|
|  | SPECIFICITY | 100.0% |

FIG. 12C

| EMBODIMENT 1 | NUMBER OF EXACT MATCHES | 596 |
|---|---|---|
|  | EXACT MATCH RATE | 99.7% |

URINE SAMPLE ANALYZER AND URINE SAMPLE ANALYZING METHOD

CROSS REFERENCE TO RELATED APPLICATIONS

This application claims priority to prior Japanese Patent Application No. 2015-169861 filed on Aug. 28, 2015 entitled "URINE SAMPLE ANALYZER AND URINE SAMPLE ANALYZING METHOD" the entire contents of which are hereby incorporated by reference.

BACKGROUND

The disclosure relates to a urine sample analyzer and a urine sample analyzing method.

There has been known an apparatus configured to classify and count particles contained in a urine sample. A urine sample collected from a patient contains a number of different particles depending on the conditions of the patient. In urine tests and disease diagnosis, it is important to count the particles contained in the urine sample.

Patent Document 1 describes a method including staining a urine sample, letting the urine sample flow through a flow cell, detecting fluorescence and scattered light generated from particles, and classifying and counting red blood cells, yeast-like fungus, and sperms based on fluorescent signal intensity and scattered light signal intensity.

Patent Document 1: Japanese Patent Application Publication No. 2007-255954

SUMMARY

In analysis of an abnormal sample containing more bacteria than normal, however, aggregates formed by aggregation of bacteria are sometimes erroneously determined as sperms. Even in analysis of such an abnormal sample, it is desired to accurately determine the presence of sperms without determining particles other than the sperms as the sperms.

A first aspect of embodiments relates to a urine sample analyzer. The urine sample analyzer according to this aspect includes: a flow cell through which a measurement specimen containing a urine sample flows; a light source that applies light onto the measurement specimen flowing through the flow cell; a light receiver that receives light from particles contained in the urine sample, and outputs a signal corresponding to the received light; and an analysis unit that determines presence of sperms in the urine sample, based on parameters reflecting a signal waveform of the signal outputted by the light receiver.

A second aspect of embodiments relates to a urine sample analyzer. The urine sample analyzer according to this aspect includes: a flow cell through which a measurement specimen containing a urine sample flows; a light source that applies light onto the measurement specimen flowing through the flow cell; a light receiver that receives light from particles contained in the urine sample, and outputs a signal corresponding to the received light; and an analysis unit that determines presence of sperms in the urine sample, based on parameters reflecting a rise time and a fall time of a waveform of the signal outputted by the light receiver.

A third aspect of embodiments relates to a urine sample analyzer. The urine sample analyzer according to this aspect includes: a flow cell through which a measurement specimen containing a urine sample flows; a light source that applies light onto the measurement specimen flowing through the flow cell; a light receiver that receives light from particles contained in the urine sample, and output a signal corresponding to the received light; a storage unit that stores a reference signal waveform representing shape characteristics of sperms; and an analysis unit that performs pattern matching between a waveform of the signal outputted by the light receiver and the reference signal waveform stored in the storage unit, and to perform determination about the presence of sperms in the urine sample, based on similarity between the both waveforms.

A fourth aspect of embodiments relates to a urine sample analyzing method. The urine sample analyzing method according to this aspect includes: letting a measurement specimen containing a urine sample flow through a flow cell; applying light to the measurement specimen flowing through the flow cell; acquiring a signal corresponding to light received from particles contained in the urine sample; and determining presence of sperms in the urine sample, based on parameters reflecting a waveform of the acquired signal.

A fifth aspect of embodiments relates to a urine sample analyzing method. The urine sample analyzing method according to this aspect includes: letting a measurement specimen containing a urine sample flow through a flow cell; applying light to the measurement specimen flowing through the flow cell; acquiring a signal corresponding to light received from particles contained in the urine sample; and determining presence of sperms in the urine sample, based on parameters reflecting a rise time and a fall time of a waveform of the acquired signal.

BRIEF DESCRIPTION OF DRAWINGS

FIG. 8 is a flowchart illustrating sperm determination processing by the urine sample analyzer according to Embodiment 1.

FIG. 10 is a flowchart illustrating display processing by the urine sample analyzer according to Embodiment 1.

FIG. 11A is a table for comparing a determination result according to a comparative example with a determination result by visual observation. FIG. 11B is a table illustrating sensitivity and specificity according to the comparative example. FIG. 11C is a table illustrating the number of exact matches and an exact match rate according to the comparative example.

FIG. 12A is a table for comparing a determination result according to Embodiment 1 with a determination result by visual observation. FIG. 12B is a table illustrating sensitivity and specificity according to Embodiment 1. FIG. 12C is a table illustrating the number of exact matches and an exact match rate according to Embodiment 1.

EMBODIMENTS

<Embodiment 1>

Embodiment 1 of a urine sample analyzer configured to analyze particles in a urine sample is described. The particles in the urine sample include red blood cells, white blood cells, sperms, yeast-like fungus, trichomonas, epithelial cells, bacteria, cast, mucus threads, crystal, and the like. The urine sample to be analyzed includes urine collected from a living body, such as primary urine, urine in the ureter, urine in the bladder, and urine in the urethra, besides discharged urine.

Figure 1:
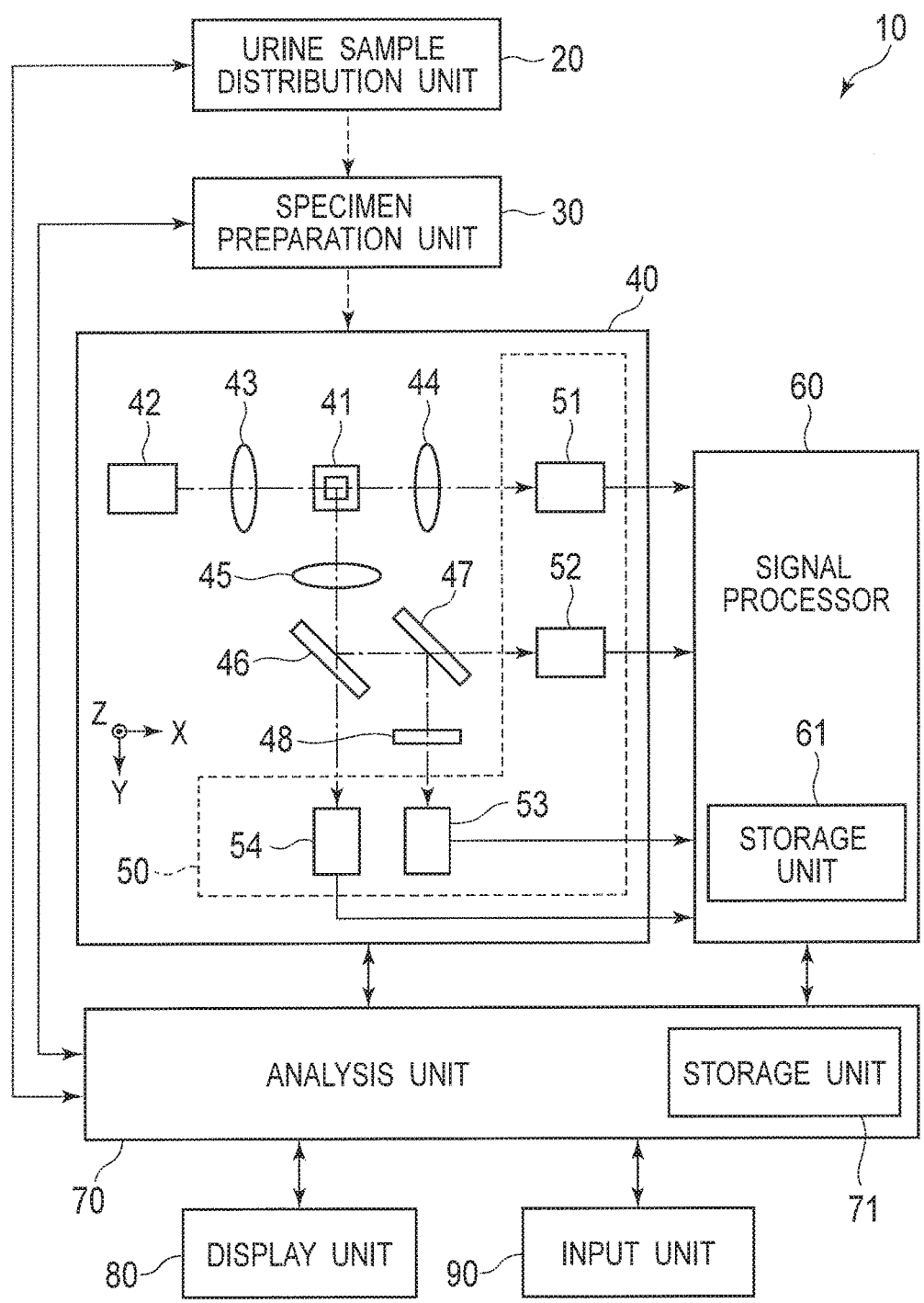
FIG. 1 is a diagram illustrating a configuration of a urine sample analyzer according to Embodiment 1.

As illustrated in FIG. 1, urine sample analyzer 10 includes urine sample distribution unit 20, specimen preparation unit 30, optical detector 40, signal processor 60, analysis unit 70, display unit 80, and input unit 90.

Figure 2:
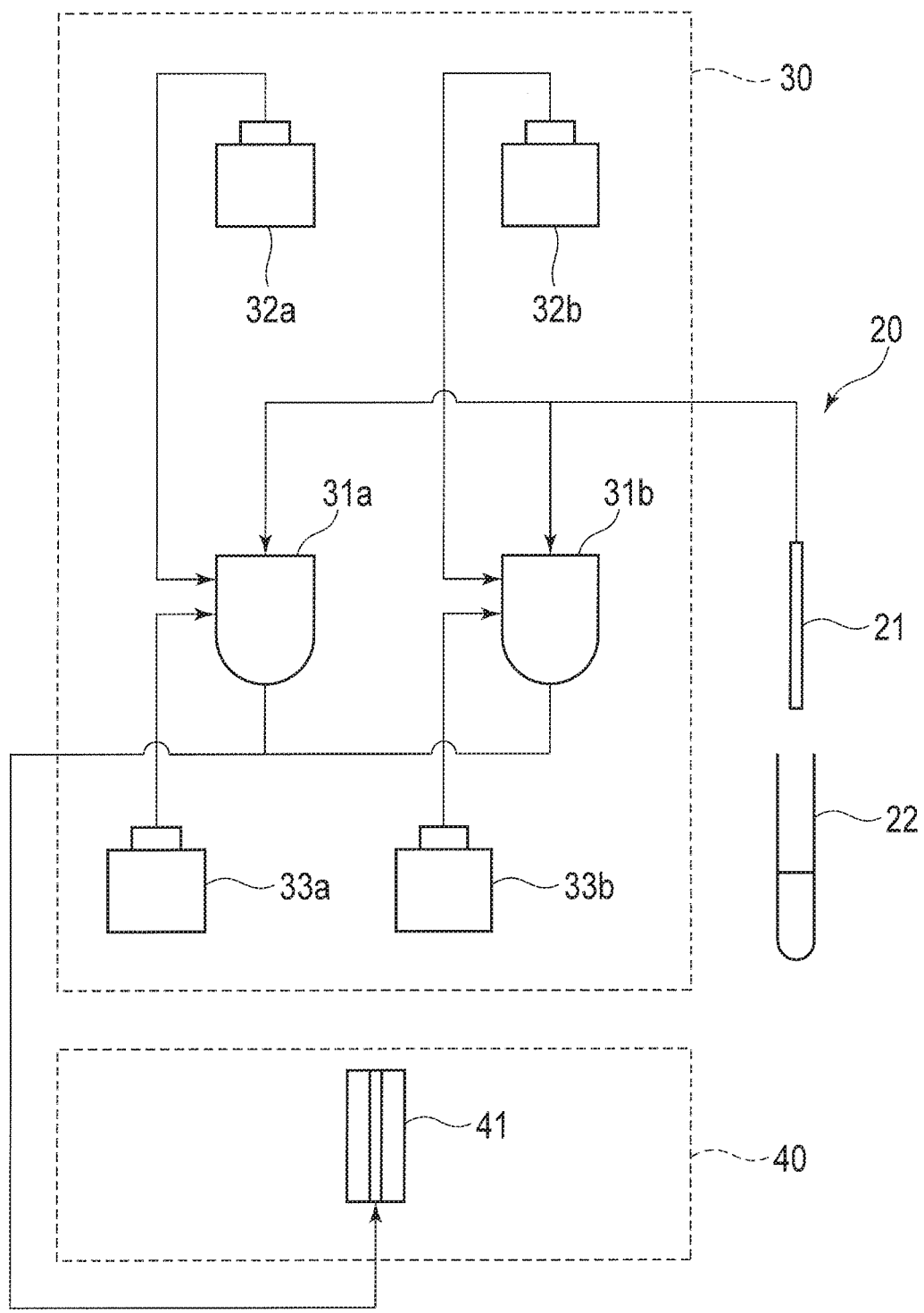
FIG. 2 is a diagram illustrating configurations of a urine sample distribution unit and a specimen preparation unit according to Embodiment 1.

As illustrated in FIG. 2, urine sample distribution unit 20 includes aspiration tube 21. Specimen preparation unit 30 includes reaction tanks 31a and 31b. Urine sample distribution unit 20 aspirates a urine sample stored in sample container 22 through aspiration tube 21. Urine sample distribution unit 20 dispenses the aspirated urine sample into reaction tanks 31a and 31b in specimen preparation unit 30. To be more specific, urine sample distribution unit 20 distributes a first portion of the urine sample into reaction tank 31a and distributes a second portion of the urine sample into reaction tank 31b. Specimen preparation unit 30 prepares measurement specimens in reaction tanks 31a and 31b.

Diluent 32a and staining solution 33a are connected to reaction tank 31a in a suppliable state. In reaction tank 31a, the first portion of the urine sample is mixed with diluent 32a and staining solution 33a. Thus, particles contained in the first portion of the urine sample are stained, and a first measurement specimen is prepared. Staining solution 33a contains a staining dye that stains cell membranes and proteins. The first measurement specimen is used to analyze particles having no nucleic acid, such as red blood cells, cast, mucus threads, and crystal in urine, and to determine the presence of sperms. Hereinafter, urine particles having no nucleic acid as a basic structure of particles, such as red blood cells, cast, mucus threads, and crystal, are referred to as non-nucleated components.

As for staining solution 33a for staining the non-nucleated components, a fluorescent dye more likely to bond to lipid and proteins of cell membranes than nucleic acid is selected. Such a dye is preferably a dye that does not affect the form of the red blood cell among cyanine dyes, styryl dyes, and acridine dyes. A dye for staining the non-nucleated components is preferably a lipophilic carbocyanine dye, more preferably, an indocarbocyanine dye, an oxacarbocyanine dye, and the like. Specific examples of the indocarbocyanine dye include DiI(1,1'-dioctadecyl-3,3,3',3'-tetramethylindocarbocyanine perchlorate), DiD(1,1'-dioctadecyl-3,3,3',3'-tetramethylindodicarbocyanine), DiR(1,1'-dioctadecyltetramethyl indotricarbocyanine Iodide), and the like. Examples of the oxacarbocyanine dye include DiOC2(3) (3,3'-diethyloxacarbocyanine iodide), DiOC3(3)(3,3-Dipropyloxacarbocyanine iodide), DiOC4(3)(3,3'-Dibutyloxacarbocyanine iodide), DiOC5(3) (3,3-Dipentyloxacarbocyanine iodide), and the like. As the staining dye contained in staining solution 33a in Embodiment 1, DiOC3(3)(3,3-Dipropyloxacarbocyanine iodide) is particularly preferable.

Diluent 32a is a reagent mainly including a buffering agent. Diluent 32a contains an osmotic pressure compensating agent so as to obtain a stable fluorescent signal without hemolyzing red blood cells. The osmotic pressure of diluent 32a is adjusted to 100 to 600 mOsm/kg so as to be suitable for classified measurement. The cell membranes or proteins of the non-nucleated components are stained by mixing the urine sample, staining solution 33a, and diluent 32a.

Diluent 32b and staining solution 33b are connected to reaction tank 31b in a suppliable state. In reaction tank 31b, the second portion of the urine sample is mixed with diluent 32b and staining solution 33b. Thus, particles contained in the second portion of the urine sample are stained, and a second measurement specimen is prepared. Staining solution 33b contains a staining dye that specifically stains nucleic acids. The second measurement specimen is used to analyze cells having nucleic acids, such as white blood cells, sperms, yeast-like fungus, trichomonas, epithelial cells, and bacteria. Hereinafter, urine particles having nucleic acids as a basic structure of particles, such as white blood cells, sperms, yeast-like fungus, trichomonas, epithelial cells, and bacteria, are referred to as nucleated components. In this regard, even having no nucleus, sperms and bacteria belong to the nucleated components since they contain nucleic acids.

As for staining solution 33b for staining the nucleated components, a fluorescent dye more likely to bond to nucleic acids than lipid and proteins is selected. To be more specific, staining solution 33b contains a dye to bond to an intercalator or a minor groove for specifically staining the nucleic acids. Examples of the intercalator include heretofore known dyes such as cyanine dyes, acridine dyes, and phenanthridium dyes. Examples of the cyanine intercalator include SYBR Green I and thiazole orange. Examples of the acridine intercalator include acridine orange. Examples of the phenanthridium intercalator include propidium iodide and ethidium bromide. Examples of the dye to bond to a minor groove include heretofore known dyes such as DAPI and Hoechst. The Hoechst dyes to bond to a minor groove include Hoechst 33342 and Hoechst 33258. The staining dye contained in staining solution 33b in Embodiment 1 is preferably the cyanine intercalator, more preferably, SYBR Green I and thiazole orange.

Diluent 32b damages the cell membrane, thereby facilitating the passage of staining solution 33b through the membrane. Also, diluent 32b contains a cationic surfactant for hemolyzing red blood cells and contracting foreign substances such as fragments of the red blood cells. Diluent 32b may contain a non-ionic surfactant rather than the cationic surfactant. By mixing the urine sample, staining solution 33b, and diluent 32b, the nucleated components are stained to the degree corresponding to the configuration and characteristics thereof.

Reaction tanks 31a and 31b are each connected to flow cell 41 in optical detector 40. The measurement specimens containing urine samples flow through flow cell 41. After the first measurement specimen in reaction tank 31a flows through flow cell 41, the second measurement specimen in reaction tank 31b flows through flow cell 41. Each of the measurement specimens forms a narrow flow enclosed in a sheath liquid in flow cell 41. Thus, particles contained in the measurement specimen pass through flow cell 41 one by one.

Referring back to FIG. 1, optical detector 40 includes flow cell 41, light source 42, condenser lenses 43 to 45, dichroic mirror 46, half mirror 47, polarizing filter 48, and light receiver 50. Light receiver 50 includes photodetectors 51 to 54. Light receiver 50 outputs a signal by receiving light from the particles contained in the urine sample. FIG. 1 illustrates X, Y, and Z axes for explaining the arrangement of the parts in optical detector 40. The X, Y, and Z axes are perpendicular to each other.

Light source 42 emits laser light having a wavelength of about 488 nm in an X-axis positive direction, thereby applying the laser light to the measurement specimen flowing through flow cell 41. Light source 42 includes a semiconductor laser light source or a gas laser light source, for example. The laser light emitted from light source 42 is linearly polarized light. Light source 42 is placed in urine sample analyzer 10 such that the polarization direction of the linearly polarized light is parallel to the flow direction of the measurement specimen in flow cell 41, i.e., parallel to the Z-axis direction. In other words, assuming that a plane perpendicular to the Z-axis direction is an incidence plane, the polarization direction of the laser light emitted from light source 42 is perpendicular to the incidence plane.

Condenser lens 43 condenses the laser light emitted from light source 42 onto the measurement specimen flowing through flow cell 41. When the laser light is applied to the measurement specimen, forward scattered light, side scattered light, and fluorescence are generated from the particles passing through the region irradiated with the laser light.

Condenser lens 44 condenses the forward scattered light generated in the X-axis positive direction of flow cell 41 onto photodetector 51. Photodetector 51 receives the forward scattered light, and outputs a forward scattered light signal corresponding to the intensity of the received forward scattered light. Photodetector 51 includes a photodiode, for example.

Condenser lens 45 condenses the side scattered light and fluorescence generated in a Y-axis positive direction of flow cell 41 onto dichroic mirror 46. Dichroic mirror 46 reflects the side scattered light and transmits the fluorescence. Non-polarizing half mirror 47 splits the side scattered light reflected by dichroic mirror 46 into two parts. Photodetector 52 receives the side scattered light transmitted through half mirror 47, and outputs a side scattered light signal corresponding to the intensity of the received side scattered light. Photodetector 52 includes a photomultiplier, for example. The side scattered light reflected by half mirror 47 enters polarizing filter 48.

Polarizing filter 48 is configured to block light in the polarization direction parallel to the Z-axis direction, and to transmit light in the polarization direction parallel to the X-axis direction. The side scattered light transmitted through polarizing filter 48 is hereinafter referred to as "depolarized side scattered light". Photodetector 53 receives the depolarized side scattered light, and outputs a depolarized side scattered light signal corresponding to the intensity of the received depolarized side scattered light. Photodetector 53 includes a photomultiplier, for example.

Here, when the laser light is applied to the particles in the measurement specimen, the polarization direction of the laser light in a portion where the components contained in the particles are distributed changes according to the optical rotation of the components. When the polarization direction of the laser light applied to the measurement specimen partially changes, the side scattered light contains light components in various polarization states. Of the side scattered light generated from the particles in the Y-direction, a proportion of light components in the polarization direction parallel to the X-axis direction, i.e., a degree of changing the initial polarization direction parallel to the Z-axis direction is determined based on the components contained in the particles. Therefore, the amount of the depolarized side scattered light passing through polarizing filter 48 and reaching photodetector 53 varies among kinds of the particles.

Photodetector 54 receives the fluorescence transmitted through dichroic mirror 46, and outputs a fluorescent signal corresponding to the intensity of the received fluorescence. Photodetector 54 includes a photomultiplier, for example.

Signal processor 60 includes circuits for processing signals and storage unit 61. Storage unit 61 includes a RAM, for example. Signal processor 60 calculates parameters for use in analysis, based on waveforms of the forward scattered light signal, side scattered light signal, depolarized side scattered light signal, and fluorescent signal outputted from light receiver 50. The waveforms of the signals outputted from light receiver 50 have shapes having signal values which change along the time axis. The parameters to be calculated from the signal waveforms are information reflecting shapes such as distortion in signal waveform and bias in peak.

To be more specific, signal processor 60 amplifies waveform electrical signals outputted from photodetectors 51 to 54 with a predetermined amplification degree. Signal processor 60 converts the amplified electrical signals into digital signals. Signal processor 60 performs predetermined signal processing on the converted digital signals to calculate parameters for each particle. The parameters to be calculated include peak values, widths, and difference sum/peak value of the signal waveforms. Also, the parameters to be calculated include parameters reflecting a rise time at the leading end side of the signal waveform and a fall time at the trailing end side thereof. The rise time is the time required for the signal waveform to rise, and is related to the gradient of the signal waveform during the rise. The fall time is the time required for the signal waveform to fall, and is related to the gradient of the signal waveform during the fall. Signal processor 60 stores the calculated parameters in storage unit 61. The parameters are described later with reference to FIGS. 3A to 3C and FIGS. 4A to 4C.

Analysis unit 70 includes a microcomputer, a CPU, and the like, and storage unit 71. Storage unit 71 includes a RAM, a ROM, a hard disk or the like. Analysis unit 70 controls the parts in urine sample analyzer 10 by transmitting and receiving signals between the parts in urine sample analyzer 10. Analysis unit 70 classifies and counts the particles based on the parameters stored in storage unit 61. Analysis unit 70 performs determination about the presence of sperms in the urine sample based on the parameters reflecting the shapes of the signal waveforms outputted from receiver 50.

Display unit 80 includes a display, and displays analysis results and the like. Input unit 90 includes a mouse and a keyboard. An operator inputs an instruction to urine sample analyzer 10 through input unit 90.

Next, description is given of the parameters to be calculated based on the signal waveform.

Figure 3A:
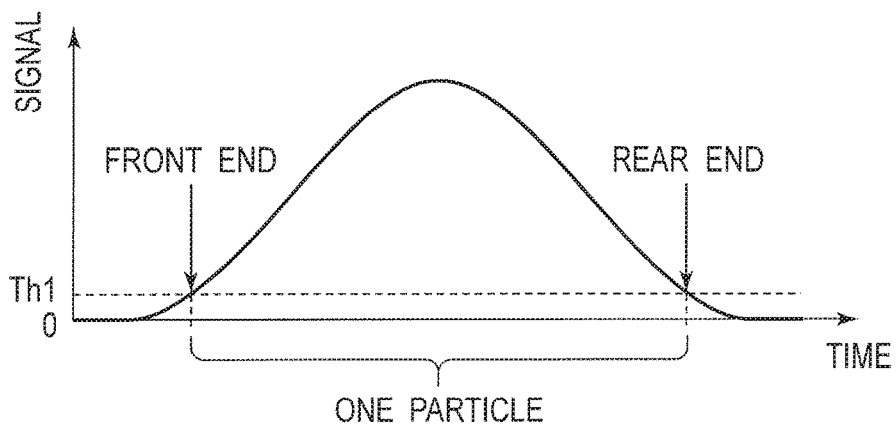
FIG. 3A is a schematic diagram illustrating a signal waveform based on one particle according to Embodiment 1.

As illustrated in FIG. 3A, the magnitude of the signal outputted from light receiver 50 changes according to the passage of the particles through the region of flow cell 41 irradiated with the laser light. Therefore, the shape of the signal waveform varies with time. The signal waveform between the time when the signal exceeds first signal threshold Th1 and the time when the signal falls below first signal threshold Th1 is regarded as a signal waveform based on one particle. In other words, first signal threshold Th1 is a signal value for specifying the signal waveform based on one particle and also specifying a rise start point and a fall end point of the signal waveform obtained from one particle. Assuming that, in the signal waveform, the point where the signal exceeds first signal threshold Th1 is the front end and the point where the signal falls below first signal threshold Th1 is the rear end, the signal waveform based on one particle extends from the front end to the rear end.

Figure 3B:
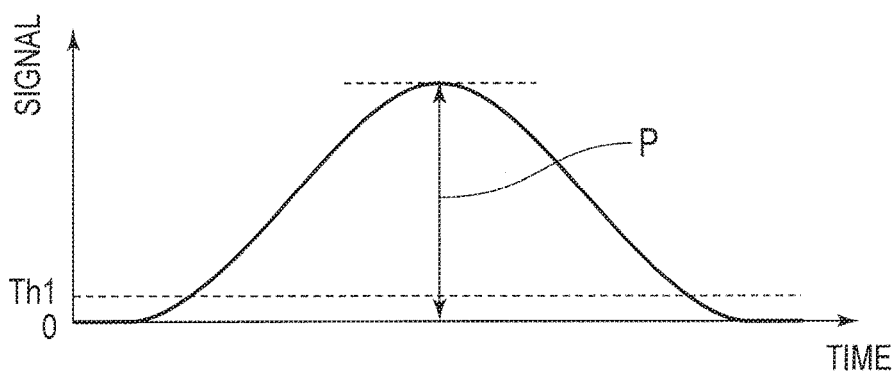
FIG. 3B is a schematic diagram illustrating a peak value of the signal waveform based on one particle according to Embodiment 1.
Figure 3C:
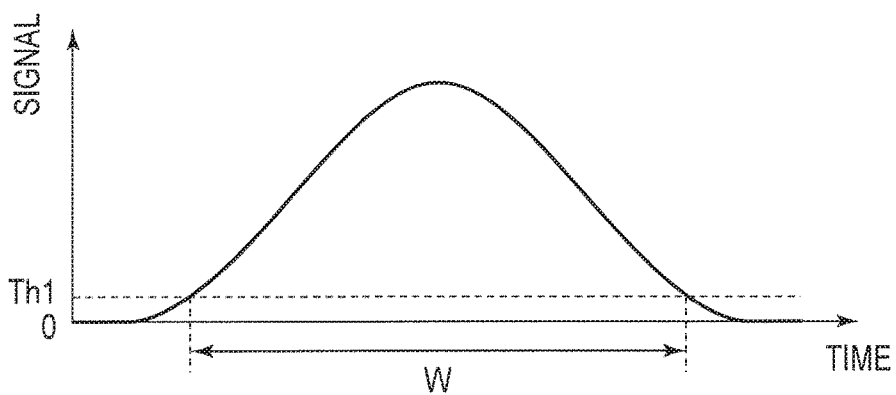
FIG. 3C is a schematic diagram illustrating a width of the signal waveform based on one particle according to Embodiment 1.

As illustrated in FIG. 3B, peak value P is the maximum value of the signal waveform based on one particle. As illustrated in FIG. 3C, width W is the width of the signal waveform based on one particle in the signal waveform. In other words, width W is a reference time between when the signal value exceeds first signal threshold Th1 and when the signal value falls below first signal threshold Th1 in the signal waveform. Moreover, the difference sum/peak value is a value obtained by dividing a sum of differences between adjacent signal values by peak value P.

Figure 4A:
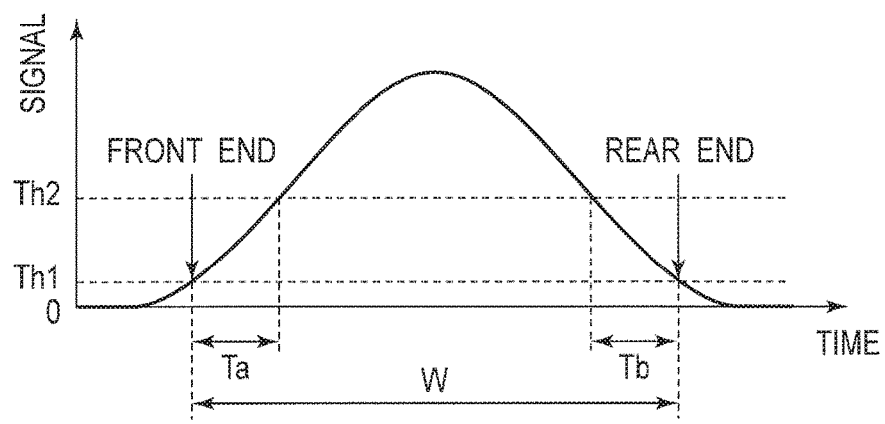
FIG. 4A is a schematic diagram for explaining a first parameter and a second parameter according to Embodiment 1.

As illustrated in FIG. 4A, second signal threshold Th2 is set to a signal value larger than first signal threshold Th1. A time period required for the signal value in the signal waveform to transition from first signal threshold Th1 to second signal threshold Th2 is set as first time Ta, and a time period required for the signal value in the signal waveform to transition from second signal threshold Th2 to first signal threshold Th1 is set as second time Tb. The rise time of the signal waveform is first time Ta, and the fall time of the signal waveform is second time Tb. A first parameter is a value obtained by dividing first time Ta by width W, while a second parameter is a value obtained by dividing second time Tb by width W. In Embodiment 1, determination about the presence of sperms in the urine sample is performed using the first and second parameters calculated based on the side scattered light signal generated from the first measurement specimen.

Figure 4B:
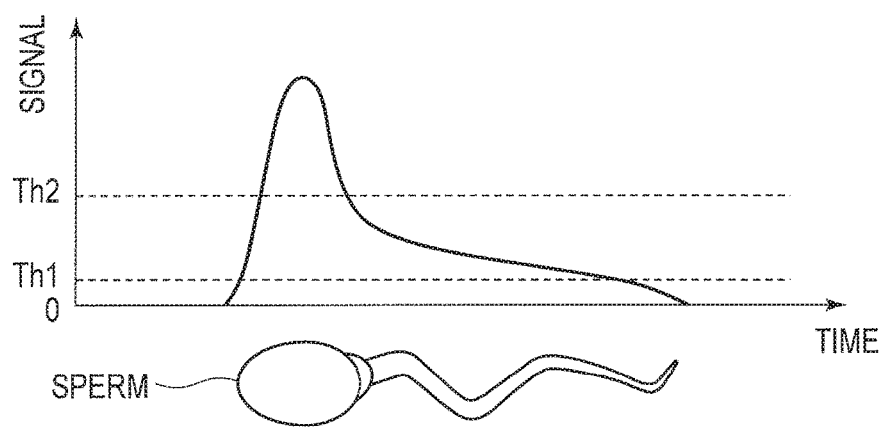
FIGS. 4B and 4C are schematic diagrams illustrating signal waveforms based on sperms according to Embodiment 1.
Figure 4C:
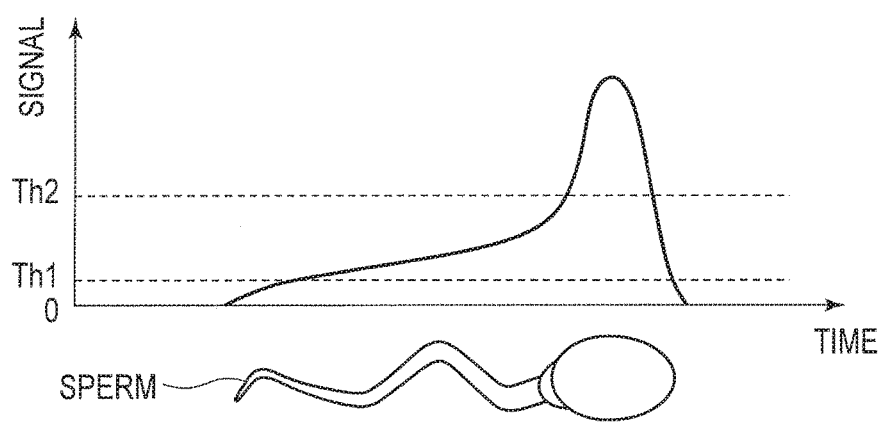

As illustrated in FIG. 4B, when a sperm contained in the first measurement specimen flows with its head first through flow cell 41, the gradient of the rise at the leading end side is increased and the gradient of the fall at the trailing end side is reduced in the signal waveform of the side scattered light. On the other hand, as illustrated in FIG. 4C, when a sperm contained in the first measurement specimen flow with its tail first through flow cell 41, the gradient of the rise at the leading end side is reduced and the gradient of the fall at the trailing end side is increased in the signal waveform of the side scattered light signal. As described above, a temporal position where the signal value of the side scattered light is increased based on the sperm is shifted to the leading end side or the trailing end side, reflecting the shape of the sperm.

Therefore, using the parameters reflecting the rise time at the leading end side of the signal waveform and the fall time at the trailing end side of the signal waveform, it can be determined whether or not the particle is the sperm. More specifically, the sperm can be extracted based on the first parameter reflecting the rise time at the leading end side of the signal waveform and the second parameter reflecting the fall time at the trailing end side of the signal waveform. To be more specific, the particle can be extracted as the sperm when the first parameter is small and the second parameter is large and when the first parameter is large and the second parameter is small. In order to enable the extraction of the sperm as described above, second signal threshold Th2 is set smaller than the peak value of the side scattered light signal of the sperm acquired from the first measurement specimen. Note that first signal threshold Th1 and second signal threshold Th2 can be arbitrarily set. For example, second signal threshold Th2 may be a value close to peak value P.

The first parameter may be the slope of a straight line connecting the point where the signal value exceeds first signal threshold Th1 and the point where the signal value exceeds second signal threshold Th2. The second parameter may be the slope of a straight line connecting the point where the signal value falls below second signal threshold Th2 and the point where the signal value falls below first signal threshold Th1.

The first and second parameters each may be a value obtained by adding a predetermined constant to a value obtained by dividing first time Ta by width W and a value obtained by dividing second time Tb by width W or may be a value obtained by multiplying such values by the predetermined constant.

Since the head and tail of the sperm are stained by the preparation of the first measurement specimen, fluorescence is generated from both of the head and tail when the laser light is applied to the sperm contained in the first measurement specimen. Therefore, the first parameter may be a value obtained by dividing first time Ta by width W based on the fluorescent signal acquired from the first measurement specimen. The second parameter may be a value obtained by dividing second time Tb by width W based on the fluorescent signal acquired from the first measurement specimen. For the extraction of the sperm, another light signal reflecting the shape of the sperm can be used other than the side scattered light signal based on the first measurement specimen.

In such a case as where urine sample analyzer 10 performs only determination about the presence of sperms, extraction of sperms may be performed based on a side scattered light signal outputted from light receiver 50 by receiving side scattered light based on a measurement specimen prepared without staining.

Figure 5:
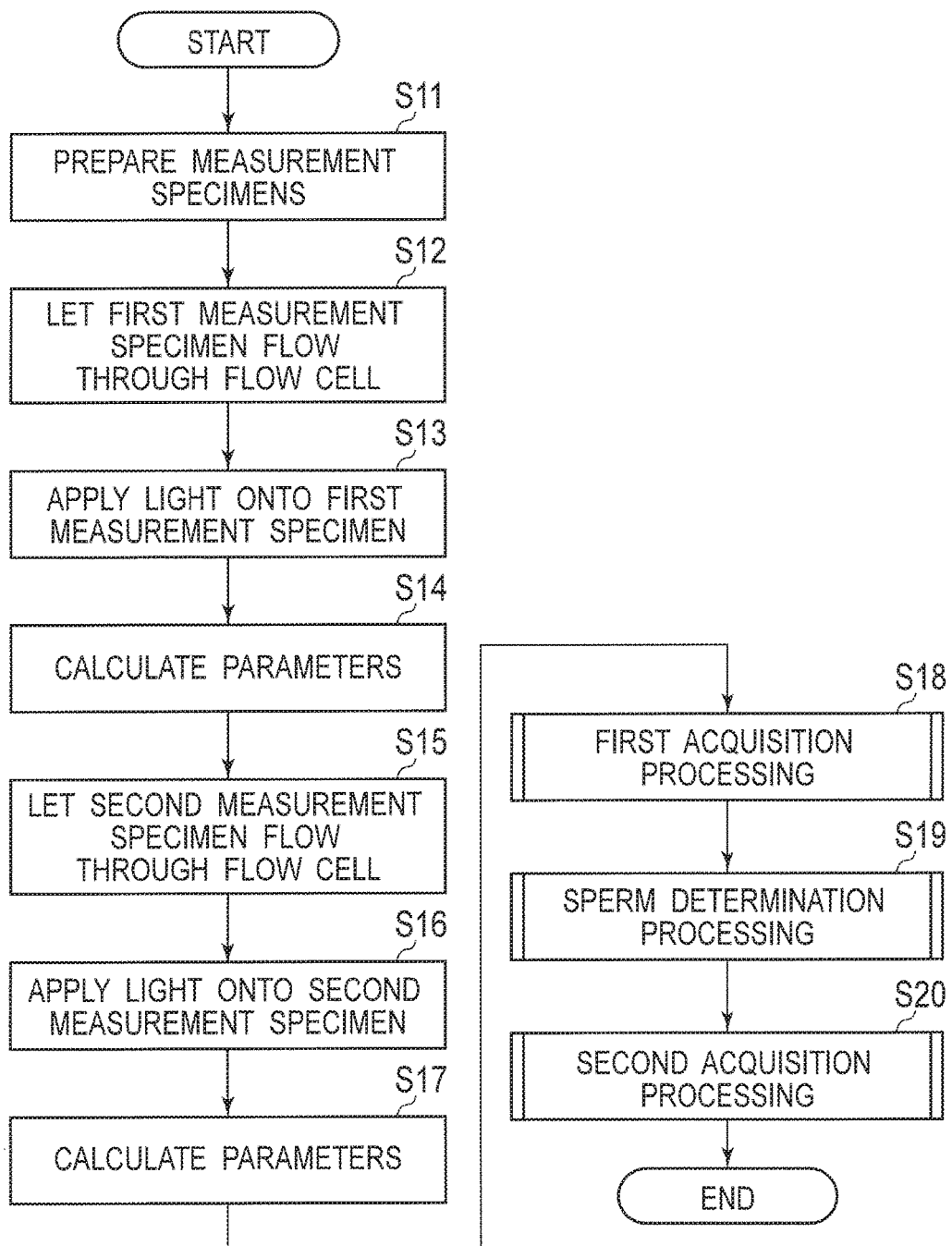
FIG. 5 is a flowchart illustrating analysis processing by the urine sample analyzer according to Embodiment 1.

Next, with reference to FIG. 5, description is given of analysis processing by urine sample analyzer 10. The analysis processing is executed by analysis unit 70 controlling the parts in urine sample analyzer 10.

In Step S11, analysis unit 70 prepares a first measurement specimen and a second measurement specimen. In Step S12, analysis unit 70 lets the first measurement specimen flow through flow cell 41. In Step S13, analysis unit 70 applies light to the first measurement specimen. In Step S14, analysis unit 70 calculates the parameters described above for each particle, based on light generated from the particle. Subsequently, in Step S15, analysis unit 70 lets the second measurement specimen flow through flow cell 41. In Step S16, analysis unit 70 applies light to the second measurement specimen. In Step S17, analysis unit 70 calculates the parameters described above for each particle, based on light generated from the particle.

In Step S18, analysis unit 70 performs first acquisition processing. In the first acquisition processing, the number of sperms is acquired based on the first measurement specimen. The first acquisition processing is described later with reference to FIG. 6. In Step S19, analysis unit 70 performs sperm determination processing. In the sperm determination processing, determination about the presence of sperms in the urine sample is performs based on the number of sperms acquired in Step S18. The sperm determination processing is described later with reference to FIG. 8. In Step S20, analysis unit 70 performs second acquisition processing. In the second acquisition processing, the number of sperms is acquired based on the second measurement specimen. The second acquisition processing is described later with reference to FIG. 9A. Analysis unit 70 stores the number of sperms acquired by the first acquisition processing, the determination result about the presence of sperms acquired by the sperm determination processing, and the number of sperms acquired by the second acquisition processing in storage unit 71.

Figure 6:
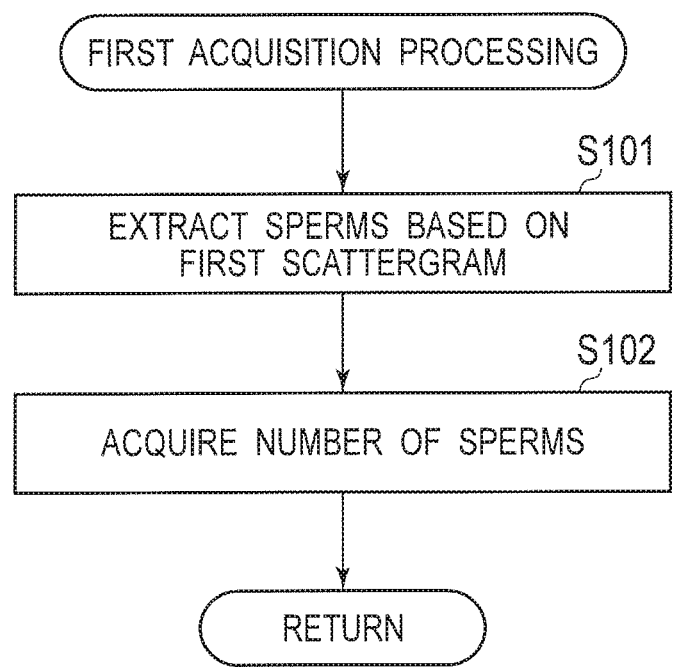
FIG. 6 is a flowchart illustrating first acquisition processing by the urine sample analyzer according to Embodiment 1.

Next, with reference to FIG. 6, the first acquisition processing is described. In the first acquisition processing, various parameters acquired from the first measurement specimen are used.

In the following description, for convenience, a scattergram is created and a range is set in the scattergram. However, creation of the scattergram and setting of the range do not always have to be performed. The particles included in the range of the scattergram may be classified and extracted by data processing.

As the first acquisition processing is started, analysis unit 70 uses the parameters of light acquired by signal processor 60 to remove in advance particles assumed to be particles other than sperms from all the particles contained in the first measurement specimen. By this preprocessing, particles assumed to be red blood cells, cast, mucus threads, crystal, white blood cells, yeast-like fungus, epithelial cells, bacteria, and the like, for example, are removed. The particles after the preprocessing are those obtained by removing such particles from all the particles contained in the first measurement specimen.

In Step S101, analysis unit 70 extracts particles corresponding to sperms from the particles after the preprocessing, based on first scattergram 110.

Figure 7A:
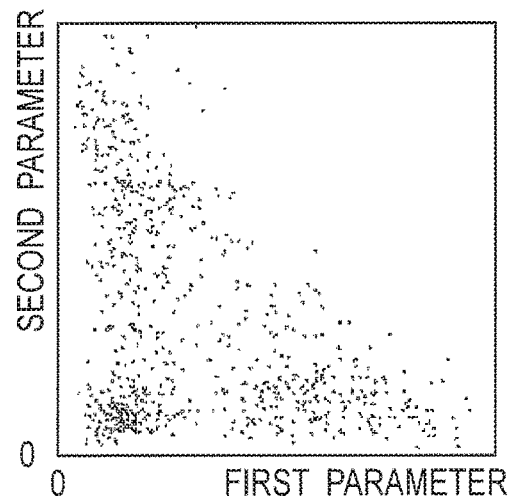
FIG. 7A is a diagram illustrating a first scattergram based on a urine sample determined to contain no sperms by visual observation according to Embodiment 1.
Figure 7B:
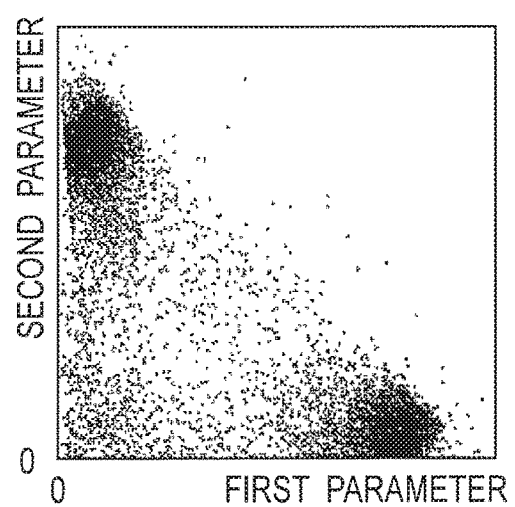
FIG. 7B is a diagram illustrating a first scattergram based on a urine sample determined to contain sperms by visual observation according to Embodiment 1.

As illustrated in FIGS. 7A and 7B, the horizontal axis of first scattergram 110 represents the first parameter, and the vertical axis thereof represents the second parameter. More specifically, the horizontal axis of first scattergram 110 represents the value obtained by dividing first time Ta by width W in the waveform of the side scattered light signal, and the vertical axis represents the value obtained by dividing second time Tb by width W in the waveform of the side scattered light signal.

Figure 7C:
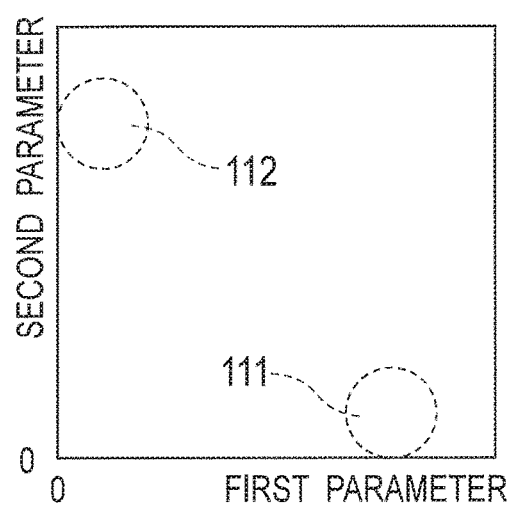
FIG. 7C is a diagram schematically illustrating a first extraction range and a second extraction range set in the first scattergram according to Embodiment 1.

Analysis unit 70 creates first scattergram 110 by plotting the particles after the preprocessing in a graph with the two parameters as the two axes. Analysis unit 70 sets first extraction range 111 and second extraction range 112 illustrated in FIG. 7C in first scattergram 110. First extraction range 111 and second extraction range 112 are ranges for surely extracting sperms based on the shape of the sperms.

As described with reference to FIGS. 4B and 4C, as for the sperms, there are cases where the first parameter is small and the second parameter is large and where the first parameter is large and the second parameter is small. Based on such a perspective, first extraction range 111 is set within a range where the first parameter is larger than the second parameter, and second extraction range 112 is set within a range where the second parameter is larger than the first parameter. First extraction range 111 corresponds to the sperm as illustrated in FIG. 4C, and second extraction range 112 corresponds to the sperm as illustrated in FIG. 4B.

As illustrated in FIGS. 7A and 7B, a urine sample determined to contain sperms by visual observation using a microscope shows numerous points characteristically distributed in first extraction range 111 and second extraction range 112 compared with a urine sample determined to contain no sperms. First extraction range 111 and second extraction range 112 are set to include just the right number of points characteristically distributed in the urine sample determined to contain sperms.

Analysis unit 70 extracts particles, for each of which a combination of the first parameter and the second parameter is found in first extraction range 111 or second extraction range 112 from the particles plotted in first scattergram 110. Thus, the particles corresponding to sperms are extracted.

In Step S101, the particles corresponding to sperms are extracted based on the shape of the sperms. Thus, the particles extracted in Step S101 become less likely to include particles other than sperms, and surely include sperms.

After the processing in Step S101, analysis unit 70 uses the parameters of light acquired by signal processor 60 to remove particles assumed to be particles other than sperms from the particles extracted in Step S101. By this post-processing, particles assumed to be bacteria, mucus threads, and the like, for example, are removed. The particles after the post-processing are those obtained by removing such particles from the particles extracted in Step S101.

In Step S102, analysis unit 70 acquires the number of the particles after the post-processing as the number of sperms. Thus, the first acquisition processing is completed.

Next, with reference to FIG. 8, the sperm determination processing is described.

In Step S201, analysis unit 70 determines whether or not the number of sperms acquired in the first acquisition processing is equal to or greater than a predetermined threshold. When the number of sperms acquired in the first acquisition processing is equal to or greater than the predetermined threshold, analysis unit 70 determines that there are sperms in the urine sample in Step S202. On the other hand, when the number of sperms acquired in the first acquisition processing is less than the predetermined threshold, analysis unit 70 determines that there are no sperms in the urine sample in Step S203.

In Step S101 of the first acquisition processing, the sperms can be surely extracted based on the shape of the sperms. Thus, in the sperm determination processing, the presence of sperms can be accurately determined based on the number of sperms acquired in the first acquisition processing.

When the presence of sperms is determined based on the first measurement specimen as described above, such determination can be performed together with analysis of particles having no nucleic acid, such as red blood cells, cast, mucus threads, and crystal, i.e., non-nucleated components. Therefore, no additional measurement specimen needs to be prepared in order to determine the presence of sperms. Thus, the amount of urine samples to be used for preparation of measurement specimens can be suppressed. Moreover, overall measurement time for urine sample analyzer 10 can be shortened.

Figure 9A:
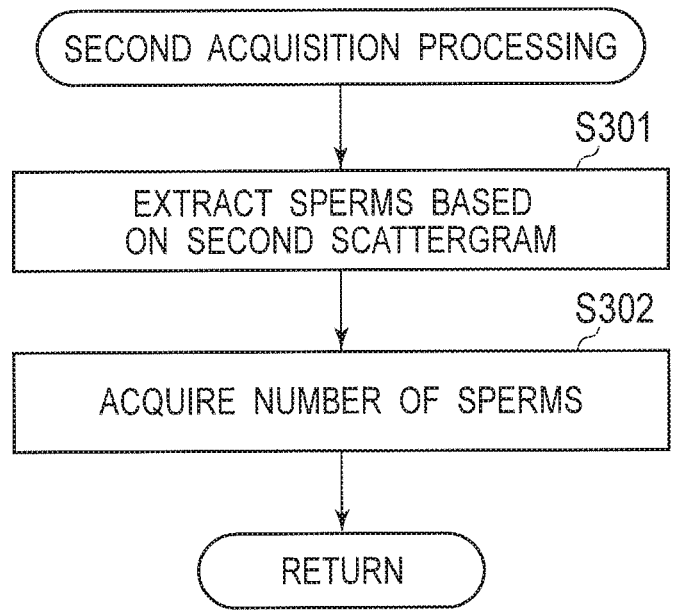
FIG. 9A is a flowchart illustrating second acquisition processing by the urine sample analyzer according to Embodiment 1.

Next, with reference to FIG. 9A, the second acquisition processing is described. In the second acquisition processing, various parameters acquired from the second measurement specimen are used.

Figure 9B:
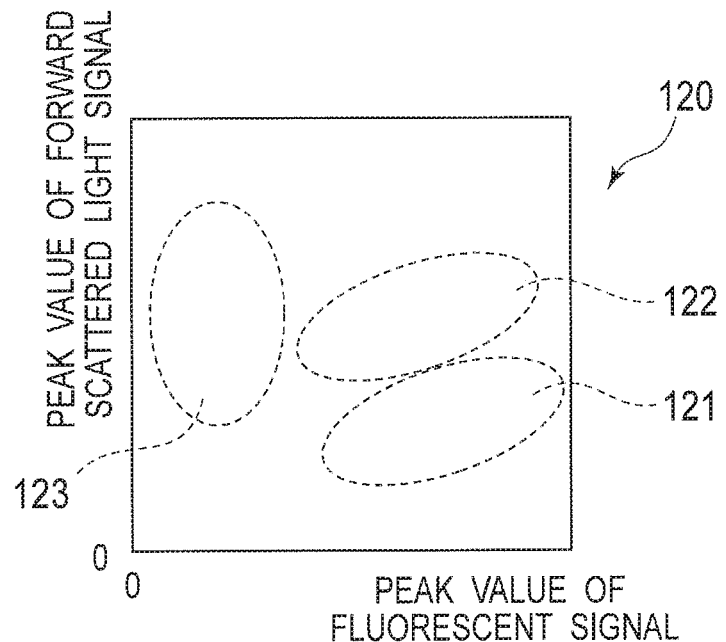
FIG. 9B is a diagram schematically illustrating a second scattergram and ranges set in the second scattergram according to Embodiment 1.

In Step S301, analysis unit 70 extracts particles corresponding to sperms from all the particles contained in the second measurement specimen, based on second scattergram 120. As illustrated in FIG. 9B, the horizontal axis of second scattergram 120 represents a peak value of the waveform of the fluorescent signal, and the vertical axis thereof represents a peak value of the waveform of the forward scattered light signal. Analysis unit 70 creates second scattergram 120 by plotting all the particles contained in the second measurement specimen in a graph with the two parameters as the two axes. Analysis unit 70 sets ranges 121 to 123 illustrated in FIG. 9B in second scattergram 120. Ranges 121 to 123 correspond to distributions of sperms, yeast-like fungus, and trichomonas, respectively. Analysis unit 70 extracts particles included in range 121 from the particles plotted in second scattergram 120. Thus, the particles corresponding to sperms are extracted.

In Step S302, analysis unit 70 acquires the number of the particles extracted in Step S301 as the number of sperms. Thus, the second acquisition processing is completed.

Next, with reference to FIG. 10, display processing by urine sample analyzer 10 is described.

In Step S401, analysis unit 70 determines whether or not a display instruction is inputted through input unit 90. When the display instruction is inputted, analysis unit 70 determines in Step S402 whether or not the determination result about the presence of sperms by the sperm determination processing is "sperms present". When the determination result about the presence of sperms is "sperms present", analysis unit 70 displays the number of sperms acquired in the second acquisition processing as the number of sperms contained in the urine sample on display unit 80 in Step S403.

In Step S403, analysis unit 70 may display the number of sperms acquired in the first acquisition processing as the number of sperms contained in the urine sample on display unit 80. However, the number of sperms is preferably the number of sperms acquired based on the second measurement specimen prepared by mixing in staining solution 33*b* that specifically stains nucleic acids, i.e., the number of sperms acquired in the second acquisition processing.

On the other hand, when the determination result about the presence of sperms is "no sperms", analysis unit 70 displays information indicating that there are no sperms in the urine sample on display unit 80 in Step S404 without displaying the number of sperms acquired in the second acquisition processing. To be more specific, analysis unit 70 displays that the number of sperms contained in the urine sample is 0 on display unit 80. Besides this, analysis unit 70 may display a message such as "urine sample contains no sperms" on display unit 80.

Based on the number of sperms acquired by the second acquisition processing, the number of sperms is 0 if it is determined by the sperm determination processing that the urine sample contains no sperms, even when the urine sample is considered to contain sperms. In other words, even when the number of sperms acquired by the second acquisition processing is improper, such an improper number of sperms acquired by the second acquisition processing is not displayed. Therefore, the processing performed as described above enables the proper number of sperms to be always displayed on display unit 80.

When the number of sperms acquired in the second acquisition processing is equal to or greater than a predetermined threshold and the determination result about the presence of sperms is "no sperms", analysis unit 70 may display a message such as "please re-examine" on display unit 80.

Next, as for actual 598 urine samples, a determination result obtained by visual observation using a microscope and a determination result according to a comparative example are compared.

In the case of the comparative example, it is determined that there are sperms when the number of sperms acquired in the second acquisition processing is equal to or greater than a predetermined threshold, while it is determined that there are no sperms when the number of sperms acquired in the second acquisition processing is less than the predetermined threshold. Likewise, in the case of the visual observation, it is determined that there are sperms when the visually counted number of sperms is equal to or greater than a predetermined threshold, while it is determined that there are no sperms when the visually counted number of sperms is less than the predetermined threshold. The determination result obtained by the visual observation is generally regarded as a proper determination result.

As illustrated in FIG. 11A, in the comparative example, it is determined for 234 urine samples that there are sperms, while it is determined for 364 urine samples that there are no sperms. On the other hand, in the visual observation, it is determined for 12 urine samples that there are sperms, while it is determined for 586 urine samples that there are no sperms.

Using the results illustrated in FIG. 11A, sensitivity and specificity are calculated. The sensitivity is a value obtained by dividing the number of urine samples determined to contain sperms in the comparative example, among the urine samples visually determined to contain sperms, by the number of the urine samples visually determined to contain sperms. The specificity is a value obtained by dividing the number of urine samples determined to contain no sperms in the comparative example, among the urine samples visually determined to contain no sperms, by the number of the urine samples visually determined to contain no sperms. As illustrated in FIG. 11B, the sensitivity is 12/12=100.0%, and the specificity is 364/586=62.1%.

Using the results illustrated in FIG. 11A, the number of exact matches and an exact match rate are calculated. The number of exact matches is the number of urine samples having the same determination result between the visual observation and the comparative example. The exact match rate is a value obtained by dividing the number of exact matches by the total number of urine samples. As illustrated in FIG. 11C, the number of exact matches is 376, and the exact match rate is 376/598=62.9%.

The results illustrated in FIGS. 11A to 11C show that, in the case of the comparative example, specificity is low, and thus there are less urine samples which can be properly determined to contain no sperms, among the urine samples which should normally be determined to contain no sperms. In other words, the results show that, in the case of the comparative example, there are many urine samples which are erroneously determined to be positive, i.e., there are many false-positive urine samples. Moreover, the results also show that, in the case of the comparative example, the exact match rate is low and there are many determination results that do not match the determination results by the visual observation.

Next, as for the same 598 urine samples as those in the case of FIGS. 11A to 11C, a determination result obtained by visual observation using a microscope and a determination result according to Embodiment 1 are compared.

In the case of Embodiment 1, as described above, it is determined that there are sperms when the number of sperms acquired by the first acquisition processing in the sperm determination processing is equal to or greater than a predetermined threshold, while it is determined that there are no sperms when the number of sperms acquired by the first acquisition processing is less than the predetermined threshold. As illustrated in FIG. 12A, in Embodiment 1, it is determined for 10 urine samples that there are sperms, while it is determined for 588 urine samples that there are no sperms.

Using the results illustrated in FIG. 12A, sensitivity and specificity are calculated. A method of calculating the sensitivity and specificity is also the same as that described above. More specifically, the sensitivity is a value obtained by dividing the number of urine samples determined to contain sperms in Embodiment 1, among the urine samples visually determined to contain sperms, by the number of the urine samples visually determined to contain sperms. The specificity is a value obtained by dividing the number of urine samples determined to contain no sperms in Embodiment 1, among the urine samples visually determined to contain no sperms, by the number of the urine samples visually determined to contain no sperms. As illustrated in FIG. 12B, the sensitivity is 10/12=83.3%, and the specificity is 586/586=100.0%.

Using the results illustrated in FIG. 12A, the number of exact matches and an exact match rate are calculated. A method of calculating the number of exact matches and the exact match rate is also the same as that described above. More specifically, the number of exact matches is the number of urine samples having the same determination result between the visual observation and Embodiment 1. The exact match rate is a value obtained by dividing the number of exact matches by the total number of urine samples. As illustrated in FIG. 12C, the number of exact matches is 596, and the exact match rate is 596/598=99.7%.

The results illustrated in FIGS. 12A to 12C show that, in the case of Embodiment 1, specificity is higher than in the comparative example, and thus there are many urine samples which can be properly determined to contain no sperms, among the urine samples which should normally be determined to contain no sperms. To be more specific, urine samples which should normally be determined to contain no sperms can all be properly determined to contain no sperms. In other words, the results show that, in the case of Embodiment 1, there is no urine sample which is erroneously determined to be positive, i.e., there is no false-positive urine sample. As described above, according to Embodiment 1, the occurrence of false positives can be suppressed.

Moreover, the results also show that, in the case of Embodiment 1, the exact match rate is higher than the comparative example and there are many determination results that match the determination results by the visual observation.

<Embodiment 2>

In Embodiment 1, the first parameter is the value obtained by dividing first time Ta by width W, and the second parameter is the value obtained by dividing second time Tb by width W. In other words, the first and second parameters in Embodiment 1 are the ratio indicating how much a portion having a high signal value is shifted to the end side in the width direction. On the other hand, in Embodiment 2, a first parameter is first time Ta and a second parameter is second time Tb. In other words, the first and second parameters in Embodiment 2 are distances of a portion having a high signal value from the leading end side and from the trailing end side in the width direction, respectively.

The first and second parameters may be values obtained by adding a predetermined constant to first time Ta and second time Tb and multiplying first time Ta and second time Tb by the predetermined constant.

In Embodiment 2, in Step S101 of FIG. 6, first scattergram 110 with first time Ta and second time Tb as two axes is created, and particles included in first extraction range 111 and second extraction range 112 are extracted as sperms. In Embodiment 2, again, sperms are distributed in the lower right range and the upper left range in first scattergram 110 as in the case of Embodiment 1. Therefore, as in the case of FIG. 7C, first extraction range 111 is set within a range where the first parameter is larger than the second parameter, and second extraction range 112 is set within a range where the second parameter is larger than the first parameter. Besides the above, configurations and control in Embodiment 2 are the same as those in Embodiment 1.

The first and second parameters in Embodiment 2 are values based on the distance rather than the ratio. Thus, sperms are randomly distributed in first scattergram 110. Therefore, first extraction range 111 and second extraction range 112 are set so as to include randomly distributed sperms. However, first extraction range 111 and second extraction range 112 in Embodiment 2 are less likely to include particles other than the sperms, which are different in size but approximately the same in ratio as the sperms. Therefore, in Step S101 of Embodiment 2, erroneous extraction of such particles other than the sperms can be suppressed. Thus, in sperm determination processing of Embodiment 2, the presence of sperms can be accurately determined based on the number of sperms acquired in first acquisition processing.

<Embodiment 3>

In Embodiment 3, determination about the presence of sperms in a urine sample is performed based on a third parameter and a fourth parameter.

Figure 13A:
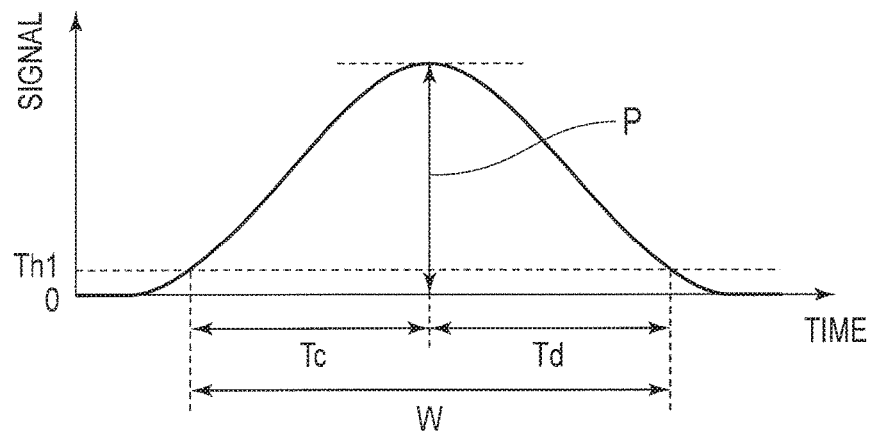
FIG. 13A is a schematic diagram for explaining a third parameter and a fourth parameter according to Embodiment 3.

As illustrated in FIG. 13A, time required for a signal value to reach the maximum value from first signal threshold Th1 in a signal waveform is third time Tc, and time required for the signal value to reach first signal threshold Th1 from the maximum value in the signal waveform is fourth time Td. The third parameter is a value obtained by dividing third time Tc by width W or a value obtained by dividing fourth time Td by width W. The fourth parameter is the maximum value of the signal waveform, i.e., peak value P. In Embodiment 3, the determination about the presence of sperms in the urine sample is performed using the third and fourth parameters calculated based on a side scattered light signal generated from a first measurement specimen.

The third parameter is the value obtained by dividing third time Tc by width W or the value obtained by dividing fourth time Td by width W, and thus can be said to be the parameter based on a temporal position where the signal value reaches its maximum in the signal waveform. The fourth parameter is peak value P of the signal waveform, and thus can be said to be the parameter based on the maximum value of the signal waveform. Therefore, the third and fourth parameters are both parameters reflecting the shape of the signal waveform, as in the case of Embodiment 1. Thus, the use of the third and fourth parameters makes it possible to determine whether or not particles are sperms and to extract the sperms, as in the case of Embodiment 1.

The third parameter may be a value obtained by adding a predetermined constant to the value obtained by dividing third time Tc by width W or the value obtained by dividing fourth time Td by width W and multiplying the values by the predetermined constant. The fourth parameter may be a value obtained by adding a predetermined constant to peak value P and multiplying peak value P by the predetermined constant.

Figure 13B:
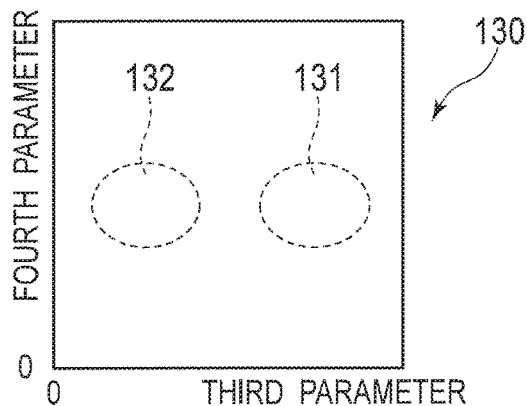
FIG. 13B is a diagram schematically illustrating a first scattergram as well as a third extraction range and a fourth extraction range set in the first scattergram according to Embodiment 3.

In Embodiment 3, in Step S101 of FIG. 6, particles corresponding to sperms are extracted from particles after preprocessing, based on first scattergram 130 illustrated in FIG. 13B. Besides the above, configurations and control in Embodiment 3 are the same as those in Embodiment 1. The processing of Step S101 in Embodiment 3 is described below.

As illustrated in FIG. 13B, the horizontal axis and vertical axis of first scattergram 130 are the third and fourth parameters based on the side scattered light signal generated from the first measurement specimen, respectively. Analysis unit 70 creates first scattergram 130 by plotting the particles after the preprocessing in a graph with the two parameters as the two axes. Analysis unit 70 sets third extraction range 131 and fourth extraction range 132 in first scattergram 130. Third extraction range 131 and fourth extraction range 132 are ranges for surely extracting sperms based on the shape of the sperms. In third extraction range 131 and fourth extraction range 132, the value of the third parameter is set in different ranges, and the value of the fourth parameter is set in approximately the same range.

When the third parameter is third time Tc/width W, third extraction range 131 corresponds to sperms in the direction illustrated in FIG. 4C, and fourth extraction range 132 corresponds to sperms in the direction illustrated in FIG. 4B. On the other hand, when the third parameter is fourth time Td/width W, third extraction range 131 corresponds to sperms in the direction illustrated in FIG. 4B, and fourth extraction range 132 corresponds to sperms in the direction illustrated in FIG. 4C.

Analysis unit 70 extracts particles, for each of which a combination of the third and fourth parameters is found in third extraction range 131 or fourth extraction range 132 from the particles plotted in first scattergram 130. In Embodiment 3, again, the particles extracted in Step S101 become less likely to include particles other than sperms, and surely include sperms. Thus, in sperm determination processing, the presence of sperms can be accurately determined based on the number of sperms acquired in first acquisition processing.

<Embodiment 4>

In Embodiment 3, the third parameter is the value obtained by dividing third time Tc by width W or the value obtained by dividing fourth time Td by width W. In other words, the third parameter in Embodiment 3 is the ratio indicating how much a portion having a high signal value is shifted to the end side in the width direction. On the other hand, in Embodiment 4, third parameters are third time Tc and fourth time Td. In other words, the third parameters in Embodiment 4 are distances of a portion having a high signal value from the leading end side and from the trailing end side in the width direction.

The third parameters may be values obtained by adding a predetermined constant to third time Tc and fourth time Td and multiplying third time Tc and fourth time Td by the predetermined constant. A fourth parameter may be a value obtained by adding a predetermined constant to peak value P and multiplying peak value P by the predetermined constant.

Figure 13C:
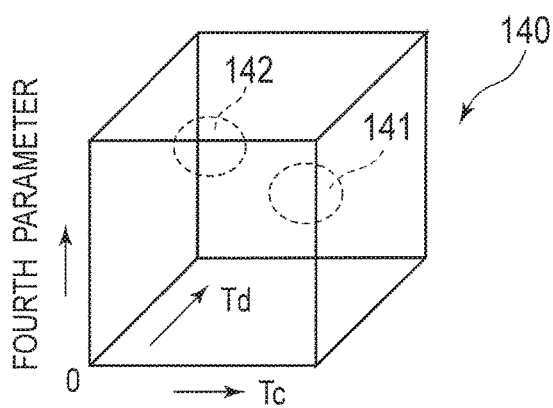
FIG. 13C is a diagram schematically illustrating a first scattergram as well as a third extraction range and a fourth extraction range set in the first scattergram according to Embodiment 4.

In Embodiment 4, in Step S101 of FIG. 6, particles corresponding to sperms are extracted from particles after preprocessing, based on first scattergram 140 illustrated in FIG. 13C. Besides the above, configurations and control in Embodiment 4 are the same as those in Embodiment 3. The processing of Step S101 in Embodiment 4 is described below.

As illustrated in FIG. 13C, first scattergram 140 is a three-dimensional scattergram including three axes perpendicular to each other. The three axes of first scattergram 140 are third time Tc, fourth time Td, and the fourth parameter indicating peak value P of the signal waveform. Analysis unit 70 creates first scattergram 140 by plotting the particles after the preprocessing in a coordinate space with the three parameters as the three axes. Analysis unit 70 sets third extraction range 141 and fourth extraction range 142 in first scattergram 140. Third extraction range 141 and fourth extraction range 142 are spatial ranges for surely extracting sperms based on the shape of the sperms.

Third extraction range 141 is set as a spatial range where third time Tc is larger than fourth time Td, while fourth extraction range 142 is set as a spatial range where fourth time Td is larger than third time Tc. Third extraction range 141 and fourth extraction range 142 are set as a spatial range where the fourth parameters are substantially the same. Third extraction range 141 corresponds to sperms in the direction illustrated in FIG. 4C, and fourth extraction range 142 corresponds to sperms in the direction illustrated in FIG. 4B.

Analysis unit 70 extracts particles, for each of which a combination of third time Tc, fourth time Td, and the fourth parameter is found in third extraction range 141 or fourth extraction range 142 from the particles plotted in first scattergram 140. In Embodiment 4, again, the particles extracted in Step S101 become less likely to include particles other than sperms, and surely include sperms. Thus, in sperm determination processing, the presence of sperms can be accurately determined based on the number of sperms acquired in first acquisition processing.

<Modified Example>

In the embodiments described above, a light signal waveform is acquired from particles contained in a urine sample, parameters reflecting the shape of the acquired light signal waveform are calculated, and particles having the calculated parameters belonging to a predetermined range are determined as sperms. However, the invention is not limited thereto. The determination about the presence of sperms may be performed using a pattern matching technique.

Figure 14A:
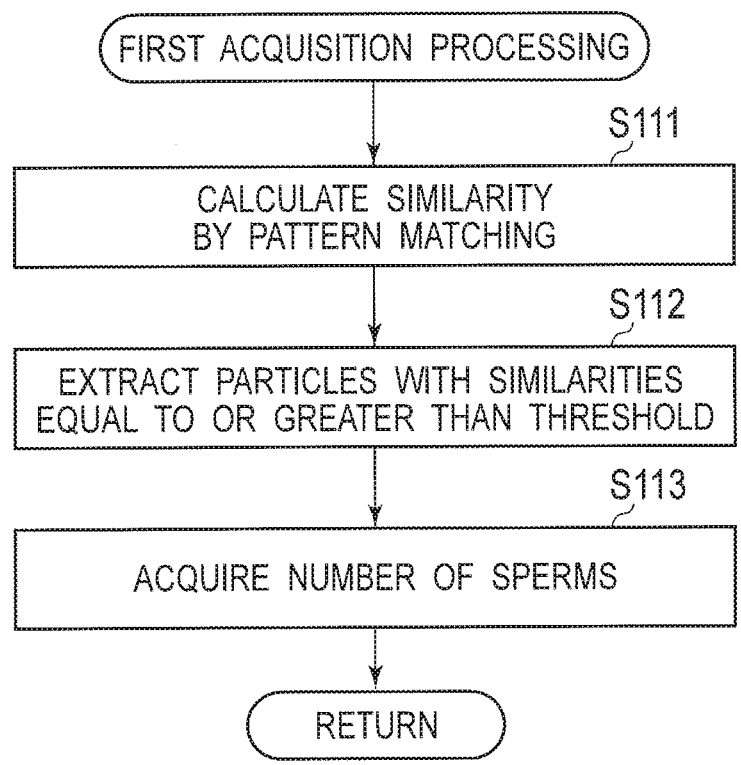
FIG. 14A is a flowchart illustrating first acquisition processing by a urine sample analyzer according to a modified example.

With reference to FIG. 14A, first acquisition processing according to a modified example is described.

Figure 14B:
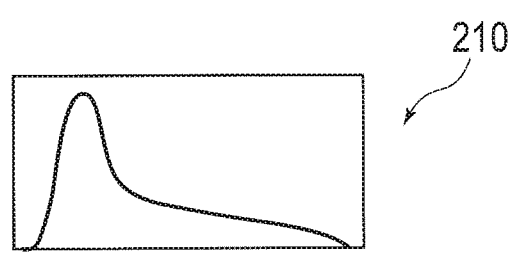
FIGS. 14B and 14C are diagrams schematically illustrating images of reference signal waveforms according to the modified example.
Figure 14C:
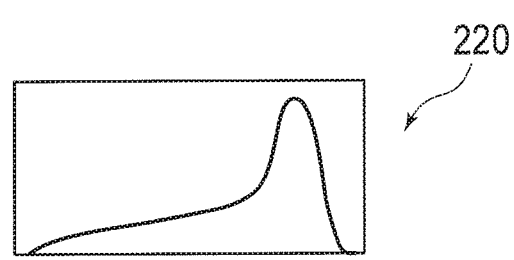

In the modified example, in Step S14 of FIG. 5, a waveform image of a side scattered light signal acquired from particles contained in a first measurement specimen is stored in storage unit 61 in signal processor 60. Also, images 210 and 220 of reference signal waveforms each indicating shape characteristics of a sperm as illustrated in FIGS. 14B and 14C are stored in storage unit 71 in analysis unit 70 in advance. Image 210 is a waveform image of a side scattered light signal typically acquired when a sperm flows with its head first through flow cell 41. Image 220 is a waveform image of a side scattered light signal typically acquired when a sperm flows with its tail first through flow cell 41.

In Step S111, analysis unit 70 calculates similarity by pattern matching. To be more specific, analysis unit 70 compares the waveform image of the side scattered light signal obtained from the particles contained in the urine sample with images 210 and 220 of the reference signal waveforms in storage unit 71, and calculates similarity between the acquired signal waveforms and the reference signal waveforms. In Step S112, analysis unit 70 extracts particles whose similarities calculated in Step S111 are equal to or greater than a predetermined threshold. In Step S113, analysis unit 70 acquires the number of the particles extracted in Step S112 as the number of sperms.

Thereafter, as in the case of Embodiment 1, in sperm determination processing, when the number of sperms acquired in the first acquisition processing of FIG. 14A is equal to or greater than a predetermined threshold, it is determined that there are sperms in the urine sample. Thus, in the modified example, again, the sperms can be surely extracted based on the shape of the sperms. Thus, in the sperm determination processing, the presence of sperms can be accurately determined.

In this way, the embodiments described above can accurately determine the presence of sperms in urine sample analysis.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A urine sample analyzer comprising:
a flow cell through which a measurement specimen containing a urine sample flows;
a light source that applies light onto the measurement specimen flowing through the flow cell;
a light receiver that receives light from particles contained in the urine sample, and outputs a signal corresponding to a magnitude of the received light; and
an analysis unit comprising a processor configured with a program to perform operations comprising:
obtaining, for each signal waveform with a peak, a first parameter representing a rise time of the signal waveform and a second parameter representing a fall time of the signal waveform;
counting particular waveforms that are to be given certain coordinates in response to being plotted on a two-dimensional plane with axes of the first parameter and the second parameter, wherein the certain coordinates comprise: (i) a group of coordinates having the first parameter relatively greater than the second parameter; and (ii) a group of coordinates having the second parameter relatively greater than the first parameter; and
determining a presence of sperms in the urine sample, based on the number of particular waveforms counted.

2. The urine sample analyzer according to claim 1, wherein
the processor is configured with the program to perform operations further comprising:
calculating the first parameter based on the rise time of the signal waveform and a reference time between a rise start and a fall end of the signal waveform, and
calculating the second parameter based on the fall time of the signal waveform and the reference time.

3. The urine sample analyzer according to claim 1, wherein
the processor is configured with the program to perform operations further comprising:
obtaining, as the rise time, a rise time on a leading end side of the signal waveform, and
obtaining, as the fall time, a fall time on a trailing end side of the signal waveform.

4. The urine sample analyzer according to claim 1, wherein
the processor is configured with the program to perform operations further comprising:
obtaining, as the rise time, a time period for a signal value in the signal waveform to transit from a first signal threshold to a second signal threshold larger than the first signal threshold, and
obtaining, as the fall time, a time period for a signal value in the signal waveform to transit from the second signal threshold to the first signal threshold.

5. The urine sample analyzer according to claim 1, wherein
the light receiver outputs a signal based on side scattered light or fluorescence, and
the first parameter and the second parameter pertain to information obtained from a signal of the side scattered light or a signal of the fluorescence.

6. The urine sample analyzer according to claim 5, wherein
the fluorescence is generated light from particles stained with a staining solution that stains cell membranes.

7. The urine sample analyzer according to claim 1, wherein
the processor is configured with the program to perform operations further comprising:
counting particles each corresponding to a signal waveform indicating shape characteristics of a sperm based on the first parameter and the second parameter, and
determining the presence of sperms in the urine sample based on a counting result.

8. The urine sample analyzer according to claim 1, further comprising:
a display unit; and
a specimen preparation unit that prepares a first measurement specimen as the measurement specimen by mixing a first portion of the urine sample with a staining solution that stains cell membranes, and prepares a second measurement specimen by mixing a second portion of the urine sample with a staining solution that stains nucleic acids, wherein
the processor is configured with the program to perform operations further comprising:
determining the presence of sperms in the urine sample based on the first measurement specimen,
acquiring the number of sperms in the urine sample based on a signal outputted from the light receiver when light from the light source is applied to the second measurement specimen flowing through the flow cell, and displaying the number of sperms acquired from the second measurement specimen on the display unit.

9. The urine sample analyzer according to claim 8, wherein the processor is configured with the program to perform operations further comprising:

displaying the number of sperms acquired based on the second measurement specimen on the display unit when sperms are determined in the urine sample based on the first measurement specimen, and not displaying the number of sperms acquired based on the second measurement specimen on the display unit when no sperms are determined in the urine sample.

10. The urine sample analyzer according to claim 9, wherein the processor is configured with the program to perform operations further comprising:

displaying information indicating that there are no sperms in the urine sample on the display unit when no sperms are determined in the urine sample based on the first measurement specimen.

11. The urine sample analyzer according to claim 1, wherein the processor is configured with the program to perform operations further comprising:

determining, in the urine sample, a presence of at least one of: blood cells, fungi, trichomonads, epithelial cells, bacteria, urinary cast, mucus threads, and crystals.

12. The urine sample analyzer according to claim 1, wherein the measurement specimen further contains a staining solution configured to stain cell membranes, and the processor is configured with the program to perform operations further comprising:

determining the presence of sperms in the urine sample, based on an interaction of the staining solution with any sperms in the urine sample and parameters reflecting the signal waveform of the signal outputted by the light receiver.

13. The urine sample analyzer according to claim 1, wherein the processor is configured with the program to perform operations further comprising:

creating a scattergram by plotting the signal waveforms on the two-dimensional plane according to coordinates determined by the first parameter and the second parameter;

setting a first extraction region encompassing (i) the group of coordinates having the first parameter relatively greater than the second parameter, and a second extraction region encompassing (ii) the group of coordinates having the second parameter relatively greater than the first parameter; and counting plots plotted in both of the first extraction region and the second extraction region.

* * * * *